United States Patent
Lu et al.

(10) Patent No.: US 11,712,417 B2
(45) Date of Patent: Aug. 1, 2023

(54) FAST DISPERSING SUSPENDING COMPOSITION, METHOD OF PREPARATION AND APPLICATION THEREOF

(71) Applicant: Auson Pharmaceuticals, Inc., Bridgewater, NJ (US)

(72) Inventors: Enxian Lu, East Brunswick, NJ (US); Peng Hou, Shanghai (CN); Longlong Feng, Shanghai (CN); Long Wang, Shanghai (CN)

(73) Assignee: AUSON PHARMACEUTICALS INC., Bridgewater, NJ (US)

( * ) Notice: Subject to any disclaimer, the term of this patent is extended or adjusted under 35 U.S.C. 154(b) by 0 days.

(21) Appl. No.: 17/805,967

(22) Filed: Jun. 8, 2022

(65) Prior Publication Data

US 2023/0190646 A1    Jun. 22, 2023

Related U.S. Application Data

(63) Continuation-in-part of application No. PCT/CN2022/076541, filed on Feb. 17, 2022.

(30) Foreign Application Priority Data

Dec. 21, 2021   (CN) .......................... 202111569644.9

(51) Int. Cl.
| | |
|---|---|
| *A61K 9/00* | (2006.01) |
| *A61K 47/26* | (2006.01) |
| *A61K 47/36* | (2006.01) |
| *A61K 47/02* | (2006.01) |

(52) U.S. Cl.
CPC ............ *A61K 9/0095* (2013.01); *A61K 47/02* (2013.01); *A61K 47/26* (2013.01); *A61K 47/36* (2013.01)

(58) Field of Classification Search
None
See application file for complete search history.

(56) References Cited

U.S. PATENT DOCUMENTS

2021/0212987 A1*   7/2021   Tyavanagimatt ...... A61K 47/26

FOREIGN PATENT DOCUMENTS

| CN | 102144975 A | 8/2011 |
| CN | 105832671 A | 8/2016 |
| CN | 111904942 A | 11/2020 |

OTHER PUBLICATIONS

Fang, Liang: "Pharmaceutical Formulations", Published Mar. 31, 2016, pp. 357-366.

* cited by examiner

*Primary Examiner* — Robert A Wax
*Assistant Examiner* — Quanglong N Truong
(74) *Attorney, Agent, or Firm* — Fox Rothschild LLP

(57) ABSTRACT

Disclosed herein is a fast-dispersing suspending composition which promotes the formation of a suspension for pharmaceutical, food and veterinary products. The composition includes a suspending agent, a diluent, and a glidant, wherein the amounts of these agents are selected to enable the dispersion of the composition and the formation of the suspension. Also disclosed are a method of forming a suspension of a solid dosage form and a method of administering the resulting suspension to a subject.

18 Claims, No Drawings

FAST DISPERSING SUSPENDING COMPOSITION, METHOD OF PREPARATION AND APPLICATION THEREOF

FIELD OF THE INVENTION

The present invention relates to a fast-dispersing suspending composition for facilitating the formation of a suspension and finds application in pharmaceutical, food and veterinary products.

BACKGROUND OF THE INVENTION

When the lowest strength of the tablet or capsule cannot meet the clinical needs of medicine, cutting or crushing tablets is often used as a supplement for the insufficient strength of the existing medicine. Cutting or crushing tablets plays an important role in addressing unmet clinical needs, especially in some special patient populations, including children, the elderly, patients requiring nasogastric tube administration and dysphagia. Currently, a lot of hospitals use machine cutting or crushing the tablets to weigh an appropriate amount of medicine for administration, but this method has some limitations. For example, machine cutting has strict requirements on the size, shape and dosage of the tablet, and the higher the strength, the better the quality, when the divided dose is ¼ or lower of the original tablets, the quality generally decreases. Furthermore, the tablet may expose to the air for long time during the cutting or crushing tablet process, which may also affect the quality of the drug. The shortcoming of cutting or crushing tablet is as the following:(1) the inaccuracy of dose; (2) the stability of cutting medicine; (3) the microbial contamination during cutting or crushing.

When the simple physical manipulation (cutting and crushing) cannot meet the administration requirements, the patient often dissolves or disperses the existing dosage form or active ingredient in a solvent (usually water); the dosage is calculated according to the volume of the added liquid. However, the viscosity of the dispersed solvent is typically low, and the active ingredients will re-aggregate and/or precipitate, resulting in the dosing errors. Currently, USP and EU pharmacopeia contain the high viscous suspending liquid (vehicle for oral suspension), and pharmacists grind the tablets into powder and add them into the suspending liquid to form a suspension. In order to ensure its stability, different types of preservatives are used, which is not children friendly. Meanwhile, grinding tablets can also cause microbial contamination and loss of drug content.

SUMMARY OF THE INVENTION

This patent document provides a preservative-free composition, which can be rapidly dispersed and dissolved in a solvent (such as water) and exhibit a desirable viscosity. The liquid system so obtained prevents the aggregation and precipitation of an active ingredient, so that active ingredient can be dissolved or uniformly dispersed in the solvent to allow dose accuracy. The system also maintains a good stability during administration.

An aspect of the patent document provides a method of dispersing a solid dosage form or an active ingredient in water and forming a suspension or a solution. The method includes: adding an active ingredient or a solid dosage form comprising an active ingredient to water; and adding a powder (solid) suspending composition to water; wherein the suspending composition is free from the active ingredient and comprises a suspending agent, a diluent, and a glidant; wherein the suspending agent, the diluent, the glidant and their respective amounts are selected so that the suspending composition under shaking by wrist action shaker at 120 rpm meets the following: the composition dissolves in water in less than 60 seconds to form a solution, and the solution exhibits a viscosity of higher than 30 cps.

Another aspect provides a suspension or solution prepared according to the methods disclosed herein. Another aspect provides a method of a solid dosage form to a subject which can be a human or an animal. The method includes preparing a suspension or solution according to the methods disclosed herein, and administering to the subject the suspension or solution.

DETAILED DESCRIPTION OF THE INVENTION

In view of the above technical problems, this patent document provides a fast dispersing composition as an auxiliary to promote suspension formation, wherein the composition includes a suspending agent, diluent, glidant and flavoring agent, wherein the content of the suspending agent is 0.5%-10% (w/w), glidant is 0.1%-5% (w/w) and diluent is 86%-96% (w/w), the residual amount is flavoring agent. The suspending agent is selected from one or more of xanthan gum, carbomer, croscarmellose sodium; wherein the diluent may be selected from one or more mixtures of maltitol, xylitol, sucrose and sorbitol. The glidant may be selected from one or both of silicon dioxide and talc. The flavoring agent includes a sweetener and/or flavor.

Further, in some embodiments of the above described suspending composition, the content of the suspending agent ranges 1.0%-6% (w/w), the glidant ranges 0.1%-3% (w/w) and the diluent ranges 87.5%-97% (w/w), and the residual amount is flavoring agent. The suspending agent is selected from one or more of xanthan gum, carbomer, and croscarmellose sodium. The diluent may be selected from one or more of maltitol, xylitol, sucrose and sorbitol. The glidant may be selected from one or both of silicon dioxide and talc. The flavoring agent includes a sweetener and/or flavor.

The objective of the present invention is to provide a composition having the following characteristics. Firstly, it is rapidly dispersible and soluble in a solvent and has a selected viscosity for preventing the aggregation and precipitation of an active ingredient, so that active ingredient can be dissolved or uniformly dispersed in the solvent to allow dose accuracy. Secondly, the resulting solution or suspension has a reasonable stability for a desirable window of administration.

Meeting the above objective, the composition disclosed herein includes a suspending agent, diluent, glidant and a flavoring agent. Each component in this composition serves a role as follows.

The suspending agent provides a specific viscosity of liquid, promoting the uniform distribution of the active ingredient.

The diluent increases the weight of the composition and contributes to accurate packaging. It also makes the suspending agent uniformly dispersed and facilitates fast dispersion and dissolution of the composition.

The glidant reduces the friction between particles and improves powder (granule) flowability.

The flavoring agent includes a sweetener and/or flavor. The flavor can be adjusted according to the needs of different populations.

Under the interaction with the diluent and glidant, the suspending agent can dissolve rapidly in the solvent to achieve a defined viscosity, which promotes the uniform distribution of the active ingredient of various forms of drug products such as tablets and capsules. Based on formulation screening, xanthan gum is selected for this composition. Xanthan gum provides a desirable viscosity when its concentration in the liquid ranges 0.05%-0.5%, preferably 0.075%-0.45%, with a selected range of particle size. In order to reduce the dispersion time, a dry mixing process can be adopted with the diluent selected in small particle sizes, however this design may result in poor flowability of powder. To resolve this issue, a glidant (silicon dioxide) can be added to improve the powder flowability, where the amount of silicon dioxide is between 0.1% to 3%.

Wherein the diluent is preferably sucrose or maltitol, and the diluent is 87.5-97% (w/w), preferably 93.8%-95.8% (w/w).

The sweetener in the flavoring agent is preferably sucralose, and the content is 0.1-2% (w/w), preferably 0.1%-1% (w/w). Sucralose is used as a sweetener in candy, food and pharmaceuticals. Oral sucralose is not absorbed and is excreted through feces.

Flavor is widely used in pharmaceutical preparations and food. There is strawberry flavor, grape flavor, orange flavor and other flavors on the market.

The composition prepared by the present invention preferably has a weight less than 5 g, and further preferably, 1.5 g for 20 ml or 25 ml liquid and 5.0 g for 50-100ml liquid.

A preferred composition of the present invention includes xanthan gum, sucrose or maltitol, colloidal silicon dioxide and sucralose, and the contents are respectively 1.0%-6% (w/w), 89%-97% (w/w), 0.5-3% (w/w), 0.1-2%(w/w), the sum of each component is 100%, further including 0.1-1% of flavor, wherein the D90 of xanthan gum is less than 0.18 mm, the D90 of sucrose or maltitol is 40-100 mesh. The ratio of xanthan gum to diluent is 1:10-1:100, preferably 1:35-1:45, and the concentration range of xanthan gum after dissolved into liquid (solvent is preferably water) is preferably 0.075%-0.45% (w/v). The weight of composition is preferably 1-5 g, more preferably 1.5-5 g.

The present invention further provides a single-dose or multiple-dose of pharmaceutical composition, wherein comprising an active ingredient and/or other pharmaceutically acceptable excipients, and the suspending composition disclosed herein.

In the composition, the proportion of diluent is relatively large, and the amount of suspending agent is relatively low. The composition demonstrates desirable flowability and blending uniformity to ensure uniform mixing of the components.

The present invention further provides a method of preparing the above described composition. The method includes the following steps:

(1). weighing a selected amount of a diluent and sieve it;

(2). weighing a selected amount of a suspending agent, a glidant and a flavoring agent and add them into blender, and mix with the diluent prepared from step (1);

(3). passing the mixture of step (2) through Comil to aid mixing;

(4). further mixing the mixture of step (3) in a blender to form a final blended mixture;

(5). filling the mixture of step (4) into a package.

The suspending composition obtained by the above process has good blending uniformity. The RSD of 10 samples is less than 3.0%, which belongs to the high standard of internal control. The RSD calculation is based on the assay of sucralose (0.5% of the composition).

The suspending composition is prepared by a direct blending process, without water and organic solvents in the process, and does not have any chemical reaction and incompatibility problems.

The present invention further provides an method of preparing a pharmaceutical suspension using the composition disclosed herein . The medicine can be either a single active ingredient, easily water soluble or water insoluble, or a common tablet, capsule, or other related formulation.

The method of preparation of a pharmaceutical suspension for patients is as follows:

(1) adding a selected amount of water into the mixing bottle, then adding a solid drug product such as tablets, and shake it until completely disperse.

(2) adding the composition described in this patent and shake it to form a homogeneous suspension.

(3) administrating all the suspension or using an oral syringe to take a selected volume of the suspension for administration.

The present invention can be used for different types or forms of drug products include immediate release tablets, dispersible tablets, orally disintegrating tablets, capsules, granules, powders, etc.

Drug products that can be prepared into a suspension with the suspending composition described in this patent include, but are not limited to, tadalafil tablets, ambrisentan tablets, enalapril tablets, captopril tablets, warfarin sodium tablets, Clopidogrel Hydrogen Sulphate Tablets, Metoprolol Tablets, Propranolol Tablets, Sildenafil Tablets, Amlodipine Besylate Tablets, Aspirin Effervescent Tablets, Spironolactone Tablets, Hydrochlorothiazide Tablets, Furosemide Tablets, Leucogen Tablets, Metronidazole Tablets, Linezolid Tablets, Levothyroxine Tablets, Phenobarbital Tablets, Prednisone Tablets, Vitamin B1/B2 Tablets, Ursodeoxycholic Acid Tablets, Inosine Tablets, Digoxin Tablets, Bosentan Tablets, Amiodarone Tablets, Prednisone Tablets, Diazepam Tablets, Fluconazole Capsules, Calcium Carbonate D3 Tablets, Pyridostigmine Bromide Tablets, Levetiracetam Tablets, Alprazolam Tablets, Cetirizine Tablets, Coenzyme Q10 Tablets, Dipyridamole Tablets, Bicyclol Tablets, Topiramate Tablets, Rifampicin Capsules, Acyclovir Tablets, Fenodipine Tablets, Repaglinide Tablets, Desmopressin Acetate Tablets, Metformin Hydrochloride Tablets, Prazosin Hydrochloride Tablets and other drugs that require lower doses or have a bitter taste or are difficult to swallow. In some embodiments, a capsule or a drug product carrier or container is opened first before releasing the content therein containing an active ingredient into water.

The present invention can also be used to prepare powder for oral suspension or solution as the following steps:

1. preparing granules or powders containing an active ingredient;

2. mixing with the suspending composition described in this patent; and 3. packing into dry unit form for oral suspension The process involves direct blending steps without using water and organic solvents and therefore does not incur chemical reactions and incompatibility problems.

Advantages of the suspending composition disclosed herein include:

1. The suspending composition rapidly disperses in a suitable amount of water to form a uniform viscous liquid for precise dispensing of solid drug product. It is also suitable for patients with difficulty swallowing and for veterinarian use.

2. The composition is packaged in unit form and can used by patients or their family members for drug dispensing without assistance from pharmacy.

3. The suspending composition can be blended with an active ingredient or a composition of the active ingredient to prepare a dry blend for suspension preparation.

4. The suspending composition can suppress unpleasant taste, for example, in herbal medicine.

5. The suspending composition does not contain water with good stability and is easy to carry.

6. The suspending composition does not contain preservatives or anti-foaming agents. The components of the composition are widely used in children's medicine and food and these amounts are below FDAIIG limits. The composition is therefore safe for use.

7. The composition contains commonly used excipients via solid phase blending without undesirable reactions and therefore provides a stable formulation.

The suspending composition of this patent document differs from conventional powder for oral suspension formation in several aspects:

1. No solid phase suspending composition has been reported. Liquid phase suspending compositions are generally used in pharmacy and therefore patient compliance is low.

2. The suspending composition of this patent document has defined ranges for concentrations for effective use and is not suitable unguided or unspecified reconstitution. Patient compliance is reasonable with suitable containers.

3. Conventional powder for oral suspension is reconstituted for single use. The suspending composition of this patent document allows for uniform dispersion and therefore multiple use.

4. Conventional powder for oral suspension has potential issues on ingredient-excipient incompatibility and product impurity. There is no such issue with the composition of the present invention.

5. Conventional powder for oral suspension generally has dispersion time of more than 1 minute and imposes no restriction on the size of xanthan gum. The suspending composition of this patent document can disperse/dissolve within 1 minute with restriction on the size of xanthan gum, which is one of the characteristics setting it apart from conventional compositions.

The suspending composition of this patent document and conventional powder for oral suspension are designed to address different technical challenges and therefore exhibit different characteristics.

Definition

The term "active ingredient" refers to a biologically active substance. Examples of active ingredients include therapeutic compounds, nutrients, minerals, proteins, botanicals, botanical extracts, vitamins, and vitamin derivatives. A therapeutic compound treats or prevents a disease or a condition in a subject. A cosmetic active ingredient is an ingredient or combination of ingredients that is/are effective to bring about a desirable change in one or more cosmetic skin or hair parameters. Examples include vitamin C, tocopherol, and sodium hyaluronate (hyaluronic acid), alpha and beta-hydroxy acids, ceramides, retinoic acid, etc. Unless otherwise noted, an active ingredient, when present in a dosage form, is in an "effective amount," which means that amount of an active ingredient that will elicit the biological or medical response of a tissue, system, animal or human that is being sought by a user or patient. In the context of a therapeutic compound, the "effective amount is also referred as a "therapeutically effective amount" which means any amount which, as compared to a corresponding subject who has not received such amount, results in improved treatment, healing, prevention, or amelioration of a disease, disorder, or side effect, or a decrease in the rate of advancement of a disease or disorder. Specific doses can be readily determined by one having ordinary skill in the art, using routine procedures. The term "effective amount" also includes within its scope amounts effective to enhance normal physiological function.

The term "dispersing" refers to breaking down, dissolving, or distributing in a liquid or solvent system a composition or a solid dosage form to form a suspension or a solution.

The term "dispersion time" refers to the time needed to dissolve a composition in a solvent (e.g. water) from the moment the composition is added to the solvent under shaking condition. One can readily determine the end point of dispersion time, when particles are no longer visually observed (or the very first timepoint when all particles of the composition disappear from the solvent).

The term "wrist action shaker" refers to a machine that simulates the shaking with a human hand, where the bottle or container being shaken is moved back and forth symmetrically in a vertical plane. The amplitude of the movement is defined by a shaking angle between a center vertical line and a side line. The side line defines the maximum swing of the bottle or container on the machine. The vertical line and the side line are in the same vertical plane and cross to form a shaking angle from where the bottle or container is being held or secured to the machine. The speed of the shaking is general defined by revolutions per minute (rpm) or number of full rotations / movement cycles per minute. Commercial wrist action shakers include for example Burrell Scientific Variable Speed Wrist Action® Shaker Model 95-AA 115V (MPN: 0757950419BDPN: 0757950419). Under the testing condition, a suspending composition is added alone into 20 ml of water to form a mixture consisting of the composition and water, and the mixture is shaken with a wrist action shaker at 120 rpm at a shaking angle 10°. It is discovered a selected combination of the suspending agent, the diluent, and the glidant (each in a particular amount) enables the composition in the mixture to dissolve under the testing condition with a desirable dispersion time and viscosity.

The term "subject" as used herein refers to a human or an animal.

EXAMPLES

Sucralose is used as a sweetener in candy, food and pharmaceuticals. Oral sucralose is not absorbed and is excreted through feces.

Flavor is widely used in pharmaceutical preparations and food flavoring agents. There is strawberry flavor, grape flavor, orange flavor and other flavors on the market.

In order to improve the taste, an appropriate amount of sucralose was added into the suspending composition in the patent.

The invention is illustrated by the following non-limiting embodiments. The embodiment adopts the 1.5 g composition weight to screen the formulation. With the increasing weight of the composition, the dispersion time will increase. Considering the compliance of the user, we set the criteria of dispersion time less than 60 seconds. In addition, in order to produce a stable uniform suspension and to facilitate dose accuracy, the viscosity of the liquid after reconstitution should be higher than 30 cps.

Example 1-Selection of Different Types of Suspending Agent

In order to form a uniform suspension and to facilitate accurate dosing, the liquid formed after dispersion must have a proper viscosity. In order to screen the optimal suspending agent, carbomer, sodium carboxymethyl cellulose, xanthan gum, povidone, hypromellose Cellulose was studied simultaneously, and the composition of formulation is shown in Table 1. For the evaluation of the liquid, 19 ml of water was added to form a viscous liquid of 20 ml. The evaluation results are shown in Table 2. D90 of xanthan gum (XANTURAL®180) is 0.18 mm; D90 of maltitol is 40 mesh, suspending agent to diluent ratio is about 1:15, silicon dioxide amount is 1% (w/w).

The dispersion time of formulation 1 (containing carbomer) and formulation 2 (containing Croscarmellose sodium) was more than 60 seconds, which did not meet the criteria. The formulations containing hypromellose and povidone (4, 5 and 6) have relatively rapid dispersing time, but they have low viscosity (<30 cp) and do not form a suitable suspension. Increasing the suspending agent amount of formulation 4, 5, and 6 will greatly increase the dispersion time, and a lot of bubbles will form. It is surprised to find that the formulation containing xanthan gum (formulation 3) could not only have suitable viscosity, but also disperse rapidly (less than 60 seconds). Therefore, xanthan gum was selected as suspending agent for further evaluation.

TABLE 1

Composition of formulation with different types of suspending agent (unit: mg)

| Composition | formulation 1 | formulation 2 | formulation 3 | formulation 4 | formulation 5 | formulation 6 |
|---|---|---|---|---|---|---|
| Maltitol | 1387.5 | 1387.5 | 1387.5 | 1387.5 | 1387.5 | 1387.5 |
| Carbomer 971 | 90 | — | — | — | — | — |
| Croscarmellose sodium | — | 90 | — | — | — | — |
| Xanthan gum | — | — | 90 | — | — | — |
| Povidone | — | — | — | 90 | — | — |
| Hypromellose E50 | — | — | — | — | 90 | — |
| Hypromellose K4M | — | — | — | — | — | 90 |
| Sucralose | 7.5 | 7.5 | 7.5 | 7.5 | 7.5 | 7.5 |
| Silicon dioxide | 15 | 15 | 15 | 15 | 15 | 15 |
| Total | 1500 | 1500 | 1500 | 1500 | 1500 | 1500 |

The process is: (all examples adopt this process)
(1) Weigh the amount of diluent and pass it through a 40-mesh sieve before use;
(2) Weigh the amount of suspending agent, glidant, and sweetener into the blender, and add the diluent from step (1), mix for 7 min at 20 rpm;
(3). The mixture of step (2) pass through Comil with screen aperture 1016 μm at speed of 3000 rpm (4). Add the mixture of step (3) to the blender and mix to form final blend, set the rotating speed 14 rpm and the mixing time 21 min; (5). The final mixture is packaged into different packages.

Example 2-Screening the Types of Xanthan Gum

Different types of xanthan gum have different particle sizes, different particle sizes may affect the blending uniformity and dispersion effect of the compositions in the present invention. In order to investigate this effect, we select XANTURAL®11K (D90=1.1 mm), XANTURAL®180 (D90=0.18 mm) and XANTURAL®75 (D90=0.075 mm) for study. The composition of formulation and evaluation results are shown in Tablets 3 and 4.

TABLE 2

Evaluation result of formulation with different types of suspending agent

| Critical Quality attributes (CQA) | | Formulation 1 | Formulation 2 | formulation 3 | formulation 4 | formulation 5 | formulation 6 |
|---|---|---|---|---|---|---|---|
| Powder | Appearance | White powder | White powder | White powder | White powder | White powder | White powder |
| | Flowability | good | good | good | good | good | good |
| Solution | Appearance (dispersion effect) | Transparent liquid | Transparent liquid | Transparent liquid | Transparent liquid | There are plenty of bubbles | There are plenty of bubbles |
| | Disperse time | 120 seconds | 105 seconds | 50 seconds | 65 seconds | 73 seconds | 70 seconds |
| | Viscosity | 1400.7 cp | 38.7 cp | 970.7 cp | 26 cp | 18 cp | 17 cp |

TABLE 3

Composition of formulation with different types of xanthan gum (unit: mg)

| Composition | Formulation 7 | Formulation 3 | Formulation 8 |
|---|---|---|---|
| Maltitol | 1387.5 | 1387.5 | 1387.5 |
| Xanthan gum (XANTURAL ®11K) | 90 | | |
| Xanthan gum (XANTURAL ®180) | | 90 | |
| Xanthan gum (XANTURAL ®75) | | | 90 |
| Sucralose | 7.5 | 7.5 | 7.5 |
| Silicon dioxide | 15 | 15 | 15 |
| Total | 1500 | 1500 | 1500 |

TABLE 4

Evaluation result of formulation with different types of xanthan gum

| Critical Quality attributes (CQA) | | Formulation 7 | Formulation 3 | Formulation 8 |
|---|---|---|---|---|
| Powder | Appearance | White powder | White powder | White powder |
| | Flowability | good | good | good |
| Solution | Appearance (dispersion effect) | Transparent liquid | Transparent liquid | Transparent liquid |
| | Disperse time | >60 seconds | 50 seconds | 57 seconds |
| | Viscosity | 833.4 cp | 970.7 cp | 942.6 cp |

The viscosity of formulation 7 (D90=1.1 mm) meets the requirements, but some xanthan gum is still not dissolved after dispersing 60 seconds. The viscosity and dispersion time of formulation 3 and 8 all meet the criteria. Therefore, D90 of Xanthan gum is required to be no more than 0.18 mm.

Example 3-Screening the Amounts of Xanthan Gum

Based on example 1 and 2 screening, XANTURAL®180 (D90=0.18 mm) is selected for the future examples. The amounts of xanthan gum will directly affect the viscosity and dispersion time, thereby affecting the suspension state of active ingredients. The effect of the xanthan gum amount on the CQA of product has been evaluated. The formulation and evaluation results are shown in Table 5 and Table 6. In all examples, the ratio of xanthan gum to diluent is 1:96-1:13.

TABLE 5

Composition of formulation with different amounts of xanthan gum (unit: mg)

| Composition | Formula 9 0.5% xanthan gum | Formula 10 1.0% xanthan gum | Formula 11 2.67% xanthan gum | Formula 12 4.33% xanthan gum | Formula 3 6.0% xanthan gum | Formula 13 7.0% xanthan gum |
|---|---|---|---|---|---|---|
| Maltitol | 1470 | 1462.5 | 1437.5 | 1412.5 | 1387.5 | 1372.5 |
| Xanthan gum | 7.5 | 15 | 40 | 65 | 90 | 105 |
| Sucralose | 7.5 | 7.5 | 7.5 | 7.5 | 7.5 | 7.5 |
| Silicon dioxide | 15 | 15 | 15 | 15 | 15 | 15 |
| Total | 1500 | 1500 | 1500 | 1500 | 1500 | 1500 |
| 20 ml liquid, xanthan gum concentration (%) | 0.0375 | 0.075 | 0.2 | 0.325 | 0.45 | 0.525 |

TABLE 6

Evaluation result of formulation with different amounts of xanthan gum

| Critical Quality attributes (CQA) | | Formulation 9 | Formulation 10 | Formulation 11 | Formulation 12 | Formulation 3 | Formulation 13 |
|---|---|---|---|---|---|---|---|
| Powder | Appearance | White powder | White powder | White powder | White powder | White powder | White powder |
| | Flowability | good | good | good | good | good | good |
| Solution | Appearance (dispersion effect) | Transparent liquid | Transparent liquid | Transparent liquid | Transparent liquid | There are plenty of bubbles | There are plenty of bubbles |
| | Disperse time | 10 seconds | 10 seconds | 10 seconds | 28 seconds | 50 seconds | 90 seconds |
| | Viscosity | <10 cp | 38.6 cp | 221.3 cp | 492.0 cp | 970.7 cp | 1491 cp |

With 0.5%-6.0% of xanthan gum in the composition, the dispersion time of all compositions is less than 60 seconds, but the viscosity of the formulation containing 0.5% xanthan gum is too low (<10 cp), which cannot form a suitable suspension. When the amount of xanthan gum was 7%, the dispersion time was 90 seconds. Therefore, the amount of xanthan gum in the composition is preferably 1.0%-6.0%, and the concentration range of xanthan gum in the liquid is preferably 0.075%-0.45% after reconstitution.

Example 4-Screening the Types of Diluent

Diluents can increase the weight of the composition, contributing to accurate packaging. Diluents can also contribute to rapid dispersion of the composition. Different types of diluents have different solubility and flowability. In this invention, some common diluents were selected for screening, such as sorbitol, sucrose, xylitol, maltodextrin, lactose and microcrystalline cellulose. The formulation composition and evaluation results are shown in the Table 7 and 8.

Example 5-Screening the Amounts of Sucrose

Sucrose can be used as a dry binder, a solubilizer or sweetener for chewable tablets or tablets, and is widely used as a diluent in food and oral liquid preparations to increase palatability and viscosity. As diluent in the present composition, different amounts of sucrose can have a direct effect on the blending uniformity and dispersion effect. The effects of 87.5%, 93.8%, 95.8% and 96.9% of sucrose on the CQA of product were evaluated respectively. The composition of formulation and evaluation results are shown in Table 9 and 10. The D90 of sucrose powder is 60-80 mesh. We need to use different weight of composition, 500 mg-2000 mg (Table 9), to do evaluation since sucrose is the major composition in the formulation. The water amount for reconstitution is constant to ensure that the concentration of xanthan gum is unchanged.

TABLE 7

Composition of formulation with different types of diluent (unit: mg)

| Composition | Formula 14 | Formula 15 | Formula 11 | Formula 16 | Formula 17 | Formula 18 | Formula 19 |
|---|---|---|---|---|---|---|---|
| Sorbitol | 1437.5 | — | — | — | — | — | — |
| sucrose | — | 1437.5 | — | — | — | — | — |
| Maltitol | — | — | 1437.5 | — | — | — | — |
| maltodextrin | — | — | — | 1437.5 | — | — | — |
| lactose | — | — | — | — | 1437.5 | — | — |
| microcrystalline cellulose | — | — | — | — | — | 1437.5 | — |
| xylitol | — | — | — | — | — | — | 1437.5 |
| Xanthan gum | 40 | 40 | 40 | 40 | 40 | 40 | 40 |
| Sucralose | 7.5 | 7.5 | 7.5 | 7.5 | 7.5 | 7.5 | 7.5 |
| Silicon dioxide | 15 | 15 | 15 | 15 | 15 | 15 | 15 |
| Total | 1500 | 1500 | 1500 | 1500 | 1500 | 1500 | 1500 |

TABLE 8

Evaluation result of formulation with different types of diluent

| Critical Quality attributes (CQA) | | Formulation 14 | Formulation 15 | Formulation 11 | Formulation 16 | Formulation 17 | Formulation 18 | Formulation 19 |
|---|---|---|---|---|---|---|---|---|
| Powder | Appearance | White powder | White powder | White powder | White powder | White powder | White powder | White powder |
| | Flowability | good | good | good | good | good | good | good |
| Solution | Appearance (dispersion effect) | Transparent liquid | Transparent liquid | Transparent liquid | small amount of undissolved ball | small amount of undissolved ball | Milky white liquid | Transparent liquid |
| | Disperse time | 12 seconds | 8 seconds | 10 seconds | >120 seconds | >120 seconds | 20 seconds | 15 seconds |
| | Viscosity | 218.7 cp | 223.5 cp | 221.3 cp | — | — | 370 cp | 266.7 cp |

The formulations containing sorbitol, sucrose, xylitol and maltitol all have a good dispersion effect and dispersion time, and form a transparent liquid; while the formulations containing maltodextrin and lactose have a long dispersion time. Although the formulation containing microcrystalline cellulose (formulation 18) disperses quickly, the suspension is not acceptable since microcrystalline cellulose cannot be dissolved. We selected the inexpensive sucrose as dilute (Formulation 15) for further research.

TABLE 9

Composition of formulation for different amounts of sucrose (unit: mg)

| Composition | Formulation 20 87.5% sucrose | Formulation 21 93.8% sucrose | Formulation 15 95.8% sucrose | Formulation 22 96.9% sucrose |
|---|---|---|---|---|
| Xanthan gum/ sucrose ratio | 1:10.9 | 1:23.4 | 1:35.9 | 1:48.4 |

TABLE 9-continued

Composition of formulation for different amounts of sucrose (unit: mg)

| Composition | Formulation 20 87.5% sucrose | Formulation 21 93.8% sucrose | Formulation 15 95.8% sucrose | Formulation 22 96.9% sucrose |
|---|---|---|---|---|
| Sucrose | 437.5 | 937.5 | 1437.5 | 1937.5 |
| Xanthan gum | 40 | 40 | 40 | 40 |
| Sucralose | 7.5 | 7.5 | 7.5 | 7.5 |
| Silicon dioxide | 15 | 15 | 15 | 15 |
| Total | 500 | 1000 | 1500 | 2000 |

TABLE 10

Evaluation result of formulation with different amounts of sucrose

| Critical Quality attributes (CQA) | | Formulation 20 | Formulation 21 | Formulation 15 | Formulation 22 |
|---|---|---|---|---|---|
| Powder | Appearance | White powder | White powder | White powder | White powder |
|  | Flowability | good | good | good | good |
|  | Blend uniformity (RSD %*) | 1.74% | 1.55% | 0.96% | 3.95% |
| Solution | Appearance (dispersion effect) | Transparent liquid | Transparent liquid | Transparent liquid | Transparent liquid |
|  | Disperse time | 8 seconds | 10 seconds | 10 seconds | 20 seconds |
|  | Viscosity | 194.7 cp | 213.3 cp | 221.3 cp | 217 cp |

*RSD: Based on the sucralose content in the samples taken from 10 different locations It has been found that the composition containing 87.5%-96.9% of sucrose has no obvious effect on viscosity, and RSD of all composition also meets the requirements (<5%). However, RSD is higher (3.95%) for the formulation containing 96.9% of sucrose, while the weight of composition containing 87.5% of sucrose is only 500 mg, which may induce large weight variability during filling into the stick pack. Therefore, the sucrose amount is selected at 87.5%-96.9%, preferably 93.8%-5.8%.

Example 6-Screening the Particle Sizes of Sucrose

Since the sucrose amount is greater than 90%, its particle size can directly affect the blending uniformity. The influence on blending uniformity by sucrose with different particle size, such as D90 20-40 mesh, 40-60 mesh, 60-80 mesh and 80-100 mesh, was investigated. The composition of formulation and evaluation results are shown in Table 11 and Table 12.

TABLE 11

Composition of formulation with different particle sizes of sucrose (unit: mg)

| Composition | Formulation 23 20-40 mesh | Formulation 24 40-60 mesh | Formulation 25 60-80 mesh | Formulation 26 80-100 mesh |
|---|---|---|---|---|
| Sucrose powder | 1437.5 | 1437.5 | 1437.5 | 1437.5 |
| Xanthan gum | 40 | 40 | 40 | 40 |
| Sucralose | 7.5 | 7.5 | 7.5 | 7.5 |
| Silicon dioxide | 15 | 15 | 15 | 15 |
| Total | 1500 | 1500 | 1500 | 1500 |

TABLE 12

Evaluation result of formulation with different particle sizes of sucrose

| Critical Quality attributes (CQA) | | Formulation 23 | Formulation 24 | Formulation 25 | Formulation 26 |
|---|---|---|---|---|---|
| Powder | Appearance | White powder | White powder | White powder | White powder |
| | Flowability | good | good | good | good |
| | Blend uniformity (RSD %) | 6.76% | 2.32% | 1.88% | 1.77% |
| Solution | Appearance (dispersion effect) | Transparent liquid | Transparent liquid | Transparent liquid | Transparent liquid |
| | Disperse time | 15 seconds | 8 seconds | 10 seconds | 10 seconds |
| | Viscosity | 221.2 cp | 223.3 cp | 223.5 cp | 226.3 cp |

The particle size of sucrose powder has direct effect on the quality of the product. When the D90 of sucrose is between 40 mesh and 100 mesh, there is no significant difference in dispersion time and viscosity, and the blending uniformity is very good. However, when D90 of sucrose is between 20 mesh and 40 mesh, the blending uniformity was unacceptable with RSD of 6.76%. Therefore, we prefer sucrose with particle size D90 in the range of 40-100 mesh.

Example 7-Screening the Amounts of Silicon Dioxide

Colloidal silicon dioxide is widely used in pharmaceuticals, cosmetics and food. Its small particle size and large specific surface area give its desired feature that can be used to improve the flowability of dry powders in many processes. It has been used as glidant in the present invention to improve the blend uniformity. RSD of sucralose is used as the marker to evaluate the blend uniformity. We examined the effect of 0%, 0.5%, 1.0%, 2.0% and 3.0% silica (Table 13) on the CQA of product (Table 14).

TABLE 13

Composition of formulation for different amounts of Silicon dioxide (unit: mg)

| Composition | Formulation 27 0% | Formulation 28 0.5% | Formulation 15 1.0% | Formulation 29 2.0% | Formulation 30 3.0% |
|---|---|---|---|---|---|
| Sucrose powder | 1452.5 | 1445 | 1437.5 | 1422.5 | 1407.5 |
| Xanthan gum | 40 | 40 | 40 | 40 | 40 |
| Sucralose | 7.5 | 7.5 | 7.5 | 7.5 | 7.5 |
| Silicon dioxide | — | 7.5 | 15 | 30 | 45 |
| Total | 1500 | 1500 | 1500 | 1500 | 1500 |

TABLE 14

Evaluation result of formulation with different amounts of Silicon dioxide

| Critical Quality attributes (CQA) | | Formula 27 | Formula 28 | Formula 15 | Formula 29 | Formula 30 |
|---|---|---|---|---|---|---|
| Powder | Appearance | White powder | White powder | White powder | White powder | White powder |
| | Flowability | good | good | good | good | good |
| | Blend uniformity (RSD %) | 5.43% | 3.21% | 0.96% | 0.94% | 0.76% |

TABLE 14-continued

Evaluation result of formulation with different amounts of Silicon dioxide

| Critical Quality attributes (CQA) | | Formula 27 | Formula 28 | Formula 15 | Formula 29 | Formula 30 |
|---|---|---|---|---|---|---|
| Solution | Appearance (dispersion effect) | Transparent liquid | Transparent liquid | Transparent liquid | Transparent liquid | Transparent liquid |
| | Disperse time | 12 seconds | 10 seconds | 10 seconds | 10 seconds | 8 seconds |
| | Viscosity | 219.3 cp | 224.4 cp | 221.3 cp | 232.2 cp | 227.3 cp |

Sucralose is only 0.5% or less in the formulation, in order to have a good blending uniformity, the powder needs to have good flowability. When the amount of colloidal silica between 0.5% and 3%, the powder has good blending uniformity, and the dispersion effect and dispersion time both meet the requirements. But in the absence of colloidal silica, the blending uniformity was unacceptable (RSD>5%) with an RSD of 5.43%. When 0.5% of colloidal silica is used, the blending uniformity does not meet the internal control (RSD<3.0%). Therefore, the preferred amount of colloidal silica is 0.5%-3%, preferably 1.0%-3.0%.

Example 8-The Composition Weight Effect on the Dispersion Time

The composition weight effect on the dispersion time was carried out based on formulation 15, and the result was shown in Table 15. As the composition weight increases, the dispersion time increases. The weight is preferably no more than 5 g in order to have dispersion time no more than 60 seconds. Therefore, the composition weight at 1.5 g-5 g is preferred.

TABLE 15

Composition of formulation of different weight (unit: mg)

| Composition | Formulation 15 1.5 g | Formulation 31 3 g | Formulation 32 5 g | Formulation 33 10 g |
|---|---|---|---|---|
| Sucrose powder | 1437.5 | 2875 | 4791.7 | 9583.3 |
| Xanthan gum | 40 | 80 | 133 | 267 |

TABLE 15-continued

Composition of formulation of different weight (unit: mg)

| Composition | Formulation 15 1.5 g | Formulation 31 3 g | Formulation 32 5 g | Formulation 33 10 g |
|---|---|---|---|---|
| Sucralose | 7.5 | 15 | 25 | 50 |
| Silicon dioxide | 15 | 30 | 50 | 100 |
| Total | 1500 | 3000 | 5000 | 10000 |
| Disperse volume | 20 ml | 40 ml | 70 ml | 140 ml |
| Disperse time | 10 seconds | 30 seconds | 60 seconds | 100 seconds |

Example 9-Formulation Containing Flavoring Agent

After the screening, each composition of the formulation has been selected. Considering the needs of patients for flavor, formulations containing flavor agent was also prepared. The composition and evaluation results are shown in the table 15 and Table 16.

TABLE 16

Composition of formulation containing flavoring agent (unit: mg)

| Composition | Formulation 34 | Formulation 35 | Formulation 36 | Formulation 37 |
|---|---|---|---|---|
| Xylitol | 1431.5 | — | — | — |
| Maltitol | — | 1431.5 | — | — |
| Sucrose | — | — | 1431.5 | — |
| Sorbitol | — | — | — | 1431.5 |
| Xanthan gum | 40 | 40 | 40 | 40 |
| Sucralose | 7.5 | 7.5 | 7.5 | 7.5 |
| Flavor | 6 | 6 | 6 | 6 |
| Silicon dioxide | 15 | 15 | 15 | 15 |
| Total | 1500 | 1500 | 1500 | 1500 |

TABLE 17

Evaluation results of composition containing flavoring agent

| Critical Quality attributes (CQA) | | Formulation 34 | Formulation 35 | Formulation 36 | Formulation 37 |
|---|---|---|---|---|---|
| Powder | Appearance | White powder | White powder | White powder | White powder |
| | Flowability | good | good | good | good |
| | Blend uniformity (RSD %) | 1.04% | 1.18% | 1.32% | 1.05% |
| Solution (20 ml) | Appearance (dispersion effect) | Transparent liquid | Transparent liquid | Transparent liquid | Transparent liquid |
| | Disperse time | 10 seconds | 10 seconds | 9 seconds | 10 seconds |
| | Viscosity | 232.2 cp | 225.3 cp | 224.4 cp | 217.7 cp |

The blending uniformity of each formulation is less than 3.0%, and the dispersion time and viscosity meet the requirements. Therefore, slightly reducing the amount of sucrose and adding a small amount of flavor will not affect the CQA of this product. The provided data only use sucrose as an example. When the product uses low-calorie maltitol or sorbitol, xylitol, etc. as diluent, the same conclusion can also be obtained.

Example of Usage

The application of the composition presented in this invention was studied with different drugs (Table 17), Table 18 presents a summary of the results.

The suspension was prepared by using the composition in this invention, the steps are shown as following:

1. Add 24 ml or 19 ml of pure water into the mixing bottle, then add one tablet into bottle, shake it to disperse drug completely;

2. Add 1.5 g of the composition (formulation 11 or 15) described in this patent, shake for 30 seconds, the final volume is about 25 ml or 20 ml, and the final concentration is shown in Table 18.

3. Take 1 ml from the top, middle and bottom of the prepared suspension respectively, and measure its content by HPLC.

TABLE 18

Drug information and final concentration of prepared suspensions

| The name of the drug | Specification | Lot number | Manufacturer | Final concentration |
|---|---|---|---|---|
| Hydrochlorothiazide Tablets | 25 mg | 20021511 | Changzhou Pharmaceutical Factory Co., Ltd | 1 mg/ml |
| Furosemide Tablets | 20 mg | 2008085 | Tianjin Lisheng Pharmaceutical Co., Ltd | 1 mg/ml |
| Spironolactone tablets | 20 mg | T20H048 | Hangzhou Minsheng Pharmaceutical Co., Ltd | 1 mg/ml |
| Captopril tablets | 25 mg | 19112214 | Changzhou Pharmaceutical Factory Co., Ltd | 1 mg/ml |
| Metoprolol tartrate tablets | 25 mg | 20201006 | Changzhou Siyao Pharmaceutical Co., Ltd | 1 mg/ml |
| Aspirin effervescent tablets | 500 mg | 1911167 | AstraZeneca Pharmaceuticals Limited | 20 mg/ml |
| Enalapril maleate tablets | 5 mg | 201002 | Shanghai Hyundai Pharmaceutical Co., Ltd | 0.2 mg/ml |
| Ambrisentan Tablets | 5 mg | 101210303 | Changzhou Hengbang Pharmaceutical Co., Ltd | 0.2 mg/ml |
| LeucogenTablets | 20 mg | 200802 | Jiangsu Jibel Pharmaceutical Co., Ltd | 1 mg/ml |
| Tadalafil Tablets | 5 mg | GC2T1011 | Qilu Pharmaceutical (Hainan) Co., Ltd | 0.2 mg/ml |
| Levothyroxine sodium tablets | 50 ug | G00S0E | Merck KGaA | 2 ug/ml |
| Amlodipine besylate tablets | 5 mg | EC7948 | Pfizer Pharmaceuticals Limited | 0.2 mg/ml |
| Prazosin Hydrochloride Tablets | 1 mg | 56200601 | Shanghai Shangyao Xinyi Pharmaceutical Factory Co., Ltd | 0.05 mg/ml |
| Propranolol hydrochloride tablets | 10 mg | 2005002 | Tianjin Lisheng Pharmaceutical Co., Ltd | 0.5 mg/ml |
| Clopidogrel bisulfate tablets | 75 mg | AA773 | Sanofi Winthrop Industrie | 3 mg/ml |
| Warfarin sodium tablets | 3 mg | 19911750 | Orion Corporation | 0.15 mg/ml |
| Atenolol tablets | 12.5 mg | 201003 | Tianjin Central Pharmaceutical Co., Ltd | 0.5 mg/ml |
| Desmopressin Acetate Tablets | 0.1 mg | S13571A | Huiling Pharmaceuticals | 0.005 mg/ml |
| Metformin hydrochloride tablets | 500 mg | ABS9801 | Sino-AMERICAN Shanghai Squibb Pharmaceutical Co., Ltd | 20 mg/ml |
| Sildenafil Tablets (EU) | 20 mg | B457608 | Pfizer Pharmaceuticals Limited | 1 mg/ml |

TABLE 19

Summary of assay and homogeneity of suspension from different drugs

| Name of drug | Formulation 11 | | Formulation 15 | |
|---|---|---|---|---|
| | Average content, % | RSD, % | Average content, % | RSD % |
| Hydrochlorothiazide Tablets | 99.8 | 2.98 | 99.6 | 2.10 |
| Furosemide Tablets | 95.9 | 2.73 | 96.4 | 1.61 |
| Spironolactone tablets | 96.0 | 1.43 | 97.1 | 1.64 |
| Captopril tablets | 95.7 | 0.79 | 96.4 | 1.22 |
| Metoprolol tartrate tablets | 97.4 | 2.11 | 97.7 | 1.74 |
| Aspirin effervescent tablets | 95.6 | 0.92 | 96.1 | 0.77 |
| Enalapril maleate tablets | 100.2 | 0.60 | 100.6 | 0.54 |
| Ambrisentan Tablets | 98.8 | 0.55 | 97.4 | 0.75 |
| LeucogenTablets | 101.2 | 1.25 | 99.7 | 1.37 |
| Tadalafil Tablets | 95.8 | 2.11 | 95.4 | 1.98 |
| Levothyroxine sodium tablets | 96.2 | 0.54 | 96.6 | 0.74 |
| Amlodipine besylate tablets | 97.4 | 2.23 | 97.7 | 2.17 |
| Prazosin Hydrochloride Tablets | 99.2 | 0.67 | 99.0 | 0.86 |
| Propranolol hydrochloride tablets | 97.5 | 1.68 | 97.3 | 1.36 |
| Clopidogrel bisulfate tablets | 102.1 | 3.16 | 103.2 | 3.25 |
| Warfarin sodium tablets | 103.5 | 0.99 | 102.4 | 0.57 |
| Atenolol tablets | 103.0 | 0.96 | 104.3 | 0.94 |
| Desmopressin Acetate Tablets | 102.8 | 2.59 | 101.0 | 2.37 |
| Metformin hydrochloride tablets | 101.2 | 0.84 | 99.8 | 0.47 |
| Sildenafil Tablets (EU) | 97.6 | 1.05 | 98.3 | 1.37 |

Table 19 shows that the assay results of the prepared suspensions are all in the range of 90.0% to 110.0%, and the homogeneity of all suspension is acceptable with RSD<5%. Therefore, the formulation 11 and 15 can be used to prepare homogenous drug suspension from various tablets, which is a good approach to obtain the low dose of tablets.

The invention claimed is:

1. A method of dispersing a solid dosage form in water to form a suspension, comprising:
   (a) adding the solid dosage form comprising an active ingredient to water; and
   (b) adding a powder suspending composition to the water;
   wherein the solid dosage form of step (a) and the powder suspending composition of step (b) are separately added to the water;
   wherein the suspending composition is free from the active ingredient and comprises a suspending agent, a diluent, and a glidant;
   wherein the suspending agent ranges from 0.5% to 10% (w/w) in the composition and is selected from the group consisting of xanthan gum, carbomer, croscarmellose sodium, and any combination thereof;
   wherein the diluent ranges from 86% to 96% (w/w) in the composition and is selected from the group consisting of maltitol, xylitol, sucrose, sorbitol, and any combination thereof;
   wherein the glidant ranges from 0.1% to 5% (w/w) in the composition and is selected from the group consisting of silicon dioxide, talc, and any combination thereof;
   wherein the suspending agent, the diluent, the glidant and their respective amounts are selected so that the suspending composition under a testing condition meets the following: the composition dissolves in water in less than 60 seconds to form a solution, and the solution exhibits a viscosity of higher than 30 cps; and
   wherein under the testing condition the suspending composition is added alone into 20 ml of water to form a mixture consisting of the composition and water, and the mixture is shaken with a wrist action shaker at 120 rpm at a shaking angle 10°.

2. The method of claim 1, wherein the composition further comprising a flavoring agent ranging from 0.1 to 2% (w/w) in the composition.

3. The method of claim 1, wherein the suspending agent is xanthan gum ranging from 1.0%-6.0% (w/w) in the composition prior to formation of the suspension.

4. The method of claim 3, wherein the xanthan gum has a particle size (D90) of no more than 0.18 mm.

5. The method of claim 3, wherein the ratio of xanthan gum to diluent ranges from 1:35 to 1:45.

6. The method of claim 3, wherein the amount of water is selected so that the xanthan gum in the suspension has a concentration ranging from 0.05% to 0.5% (w/v).

7. The method of claim 4, wherein the diluent is sucrose ranging from 93.8%-95.8% (w/w) in the composition.

8. The method of claim 7, wherein the diluent has a particle size (D90) ranging from 40 to 100 mesh.

9. The method of claim 8, wherein the glidant is silicon dioxide ranging from 0.5%-3% (w/w) in the composition.

10. The method of claim 1, wherein the composition ranges from 1.5 to 5.0 g.

11. The method of claim 1, wherein the volume of water ranges from 20 to 100 ml.

12. The method of claim 1, wherein the solid dosage form is a tablet, granule or powder.

13. The method of claim 1, wherein step (a) proceeds prior to step (b).

14. The method of claim 1, wherein the composition is free from a preservative.

15. The method of claim 1, wherein the suspension is suitable for multiple administrations.

16. The method of claim 1, wherein the suspending agent, the diluent, the glidant and their respective amounts are selected so that the powder suspending composition exhibits a blend uniformity of less than 5%.

17. A suspension prepared according to the method of claim 1.

18. A method of administering a solid dosage form to a subject, comprising
   (a) preparing a suspension according to the method of claim 1; and
   (b) administering to the subject the suspension.

* * * * *